(12) United States Patent
Safari et al.

(10) Patent No.: US 6,820,878 B2
(45) Date of Patent: Nov. 23, 2004

(54) MEDICAL DEVICE TRANSPORTATION UNIT

(76) Inventors: Hamid Safari, 17045 Germain St., Granada Hills, CA (US) 91344; Selina C. Safari, 17045 Germain St., Granada Hills, CA (US) 91344

( * ) Notice: Subject to any disclaimer, the term of this patent is extended or adjusted under 35 U.S.C. 154(b) by 145 days.

(21) Appl. No.: 10/222,541

(22) Filed: Aug. 16, 2002

(65) Prior Publication Data

US 2004/0032102 A1 Feb. 19, 2004

(51) Int. Cl.$^7$ ............................................. A63B 19/02
(52) U.S. Cl. ................................. 280/47.26; 280/47.19; 280/79.3; 16/114.1
(58) Field of Search ....................... 211/194, 88.01; 248/129, 460; 16/114.1, 410, 416; 190/18 A, 39; 312/233, 249.1, 249.11, 249.8, 249.12, 249.13; 280/47.26, 47.19, 47.18, 47.27, 79.2, 79.3, 37, 8, 35, 47.35, 47.315, 47.17, 638, 659, 47.24, 47.29, 655.1

(56) References Cited

U.S. PATENT DOCUMENTS

| | | | | |
|---|---|---|---|---|
| 1,649,065 A | * | 11/1927 | Jarvis et al. ............... | 280/79.2 |
| 2,667,397 A | * | 1/1954 | Hallisey ................... | 312/249.8 |
| D182,716 S | * | 5/1958 | Ferguson ..................... | D34/21 |
| 3,179,270 A | * | 4/1965 | Taragos ...................... | 414/446 |
| 4,118,048 A | * | 10/1978 | Spranger et al. ......... | 280/47.35 |
| 5,042,664 A | | 8/1991 | Shyr | |
| 5,295,565 A | | 3/1994 | Latshaw | |
| 5,566,961 A | * | 10/1996 | Snell et al. ............... | 280/47.35 |
| 5,590,779 A | | 1/1997 | Ramsey | |
| 5,676,223 A | | 10/1997 | Cunningham | |
| 5,765,842 A | * | 6/1998 | Phaneuf et al. .......... | 280/47.35 |
| 5,797,612 A | * | 8/1998 | Buccioni ................. | 280/47.26 |
| 5,906,381 A | * | 5/1999 | Hovatter .................. | 280/47.18 |
| 6,009,995 A | | 1/2000 | Speck | |
| 6,036,203 A | * | 3/2000 | Tyus et al. ............... | 280/47.26 |
| 6,076,641 A | | 6/2000 | Kinzer et al. | |
| 6,123,344 A | * | 9/2000 | Clegg ....................... | 280/47.19 |
| 6,254,112 B1 | * | 7/2001 | Clegg ....................... | 280/47.19 |
| 6,612,412 B2 | * | 9/2003 | Sanderson et al. ........ | 190/18 A |
| 6,626,445 B2 | * | 9/2003 | Murphy et al. .......... | 280/47.34 |
| 6,663,202 B2 | * | 12/2003 | Spann .................... | 312/249.12 |
| 2001/0030403 A1 | * | 10/2001 | Johnson et al. .......... | 280/47.26 |
| 2001/0045718 A1 | * | 11/2001 | Boirum ................... | 280/47.26 |
| 2002/0096844 A1 | * | 7/2002 | Clegg ....................... | 280/47.17 |
| 2003/0141687 A1 | * | 7/2003 | Wixted et al. ........... | 280/47.35 |
| 2003/0201699 A1 | * | 10/2003 | Hong et al. ................ | 312/290 |

* cited by examiner

Primary Examiner—Christopher P. Ellis
Assistant Examiner—J. Allen Shriver
(74) Attorney, Agent, or Firm—Birch, Stewart, Kolasch & Birch, LLP; Sanford Astor

(57) ABSTRACT

A medical device transportation unit comprising an upper compartment, a center compartment and a lower compartment, all said compartments having a front panel, a rear panel and two opposite side panels, a grated shelf between said upper compartment and said center compartment, a grated shelf between said center compartment and said lower compartment, the front panel of said upper compartment, the front panel of said lower compartment and all four panels of said center compartment being removably attached.

13 Claims, 3 Drawing Sheets

MEDICAL DEVICE TRANSPORTATION UNIT

This invention is described in our Disclosure Document No. 513217 filed in the Patent Office on Jun. 5, 2002.

BACKGROUND OF THE INVENTION

This invention comprises a medical device transportation unit for holding a variety of medical devices used by patients who suffer from illnesses or disorders that require them to travel with a medical device. One example of such a device is a continuous positive airway pressure machine, used to treat certain sleep disorders.

According to the American Academy of Sleep Medicine in Rochester, Minn., at least 84 disorders of sleeping and waking cause a lower quality of life by reducing personal health. It is estimated that in the United States, 20 million people have obstructed sleep apnea, most commonly diagnosed as a sleep disorder. Obstructive Sleep Apnea (OSA) is the inability to breathe during normal sleep. A person's airway is held open by muscles controlling the tongue and soft palate. As the muscle relaxes, the airway becomes narrowed, and/or blocked, causing the individual to snort or gasp for air.

As a result of obstructive sleep apnea, many individuals may be awakened several times a night, causing severe sleep deprivation and daytime sleepiness. Untreated OSA may lead to serious health problems, including but not necessary limited to, high blood pressure, heart attack, stroke, road accidents, memory loss and sexual dysfunction. Other signs and/or symptoms include morning headaches or mood swings.

OSA is not limited to adults. Children may also be affected by this disorder. Children who struggle to breathe while snoring may be suffering from OSA. Again, the child may snort or gasp and as they snore, the child starts and stops breathing.

Some of the commonalities of OSA for both adults and children include, sleeping with the head of the bed propped up with many pillows, snoring loudly and often, stopping breathing during the night for short periods of time, sweating heavily during the night, sleeping restlessly, difficulty waking up, even though he or she has had enough sleep, headaches during the day, specifically in the morning, irritability, crankiness and day dreaming in school or at work.

The only way to detect and/or determine OSA is for the specialist to record the individual's sleep for at least one night in a laboratory, with a test called polysomnography (PSG). By placing recording devices on the individual's head and body, this will monitor sleep patterns. Specialists will also monitor and record brain waves, leg and arm movements, muscle activity, heartbeat and breathing pattern.

Treatment options include surgery, nasal continuous positive airway pressure devices and life style changes. For children with enlarged tonsils, the doctor may recommend an Aden tonsillectomy, (removing of the tonsils) or uvuloplatopharyngoplasty, (uvula, tonsils and part of the soft palate are removed). A tracheotomy, (opening a hole in the wind pipe at the neck) is generally used only for life threatening situations.

Other treatments include CPAP (Continuous Positive Airway Pressure) and BiPAP (Bi-level) machine treatment, in which a small mask is worn over the nose during sleep. The machine provides air pressure to the mask that keeps the throat from closing during sleep. This is very significant for both adults and children when surgical treatment is not possible or desirable, or when surgery does not cure the OSA. By preventing airway blockage and collapse, many of the symptoms associated with OSA are alleviated.

A serious concern for the individual is the transporting and/or storing of the CPAP/BiPAP machines; which must be used continuously by the individual in order to function daily. CPAP/BiPAP users complain about storage of the machines. In hotels, many times there are limited outlets. These outlets are often being used for the hotel's appliances such as lamps, and television sets. Another concern is where to place the equipment at night. The hoses of the machine can become tangled and/or kinked during sleep, which interferes with the airflow, disturbing one's sleep. Some users are concerned that friends and or relatives may see the machine. This is embarrassing to the user. When traveling on an airplane, the user must carry the machine in a shoulder bag, which is very heavy. In addition the machine can become damaged if thrown around in the storage compartment of the plane.

While OSA has been discussed in detail, other illnesses and medical conditions also require the use of a treatment machine, for instance, portable suction machines for the treatment of tracheotomy and paraplegic patients, portable oxygen tanks and equipment for lung diseases, nebulizer machines for quadriplegic and paraplegic patients or patients who continuously receive oxygen and humidifiers for asthma patients. All of these machines and devices require the patient to transport them when traveling with the same problems described for the OSA machines.

BRIEF SUMMARY OF THE INVENTION

This invention comprises a three compartment transportation unit for a medical device, the size of a carry-on piece of luggage, which has wheels so that it can easily be transported. The upper compartment, if used for a CPAP/BiPAP machine, is used for the breathing mask and hose. The center compartment holds the blower of the machine, which in use gets very hot, and the lower compartment holds the electrical components including for instance, an extension cord and a multi-plug adaptor. There is also sufficient room in the lower compartment to store some clothing or nightwear or other items.

The four sides of the transportation unit around the center compartment, which holds the machine or blower, are totally removable, to allow proper cooling of the blower.

The floor of both the upper compartment and the center compartment are grills, allowing the easy tying down of the blower, or other machine. There is also an opening in each of the grills for passage of any hoses or wires from one compartment to the other.

The transportation unit of this invention provides the solution to the transporting, protection, and storage of a medical device, such as a CPAP/BiPAP machine, which provides great convenience for the patient, user, as well as providing storage that does not reveal the contents and the medical use of the machine, protecting the patient's privacy.

OBJECTS OF THE INVENTION

Accordingly, several objects and advantages of the invention are as follows:

It is an object of the present invention to provide a medical device transporting unit, adapted to transport a treatment machine and its attendant requirements.

Another object of the invention is to provide a medical device transporting unit which may be carried onto an airplane but holds the medical device securely and privately.

These, as well as other objects of the invention, will become obvious from the following description in which:

BRIEF DESCRIPTION OF THE DRAWINGS

FIG. 3 is an open perspective view; and

DETAILED DESCRIPTION OF THE INVENTION

Figure 1:
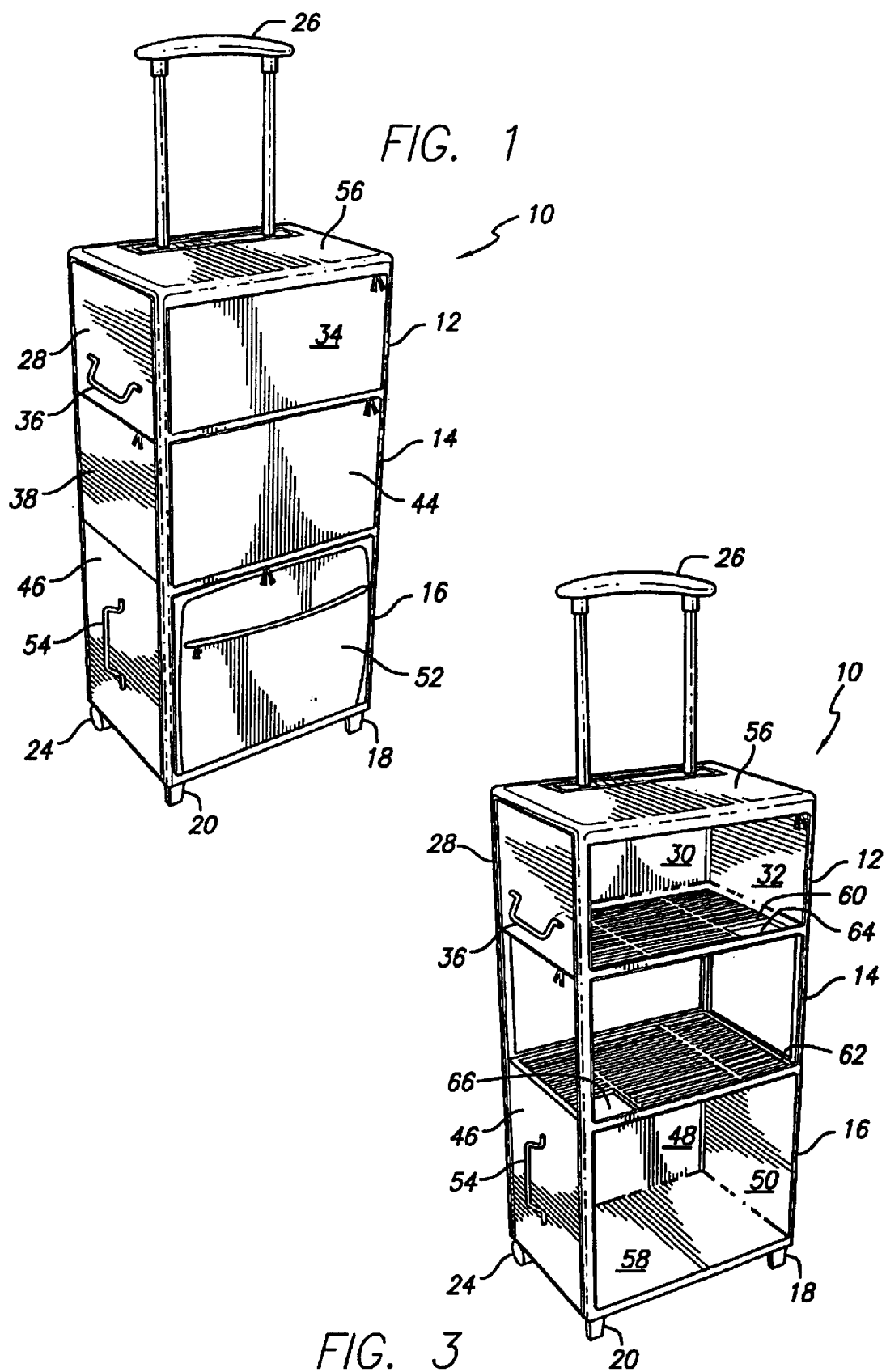
FIG. 1 is a perspective view of the transporting unit.
Figure 2:
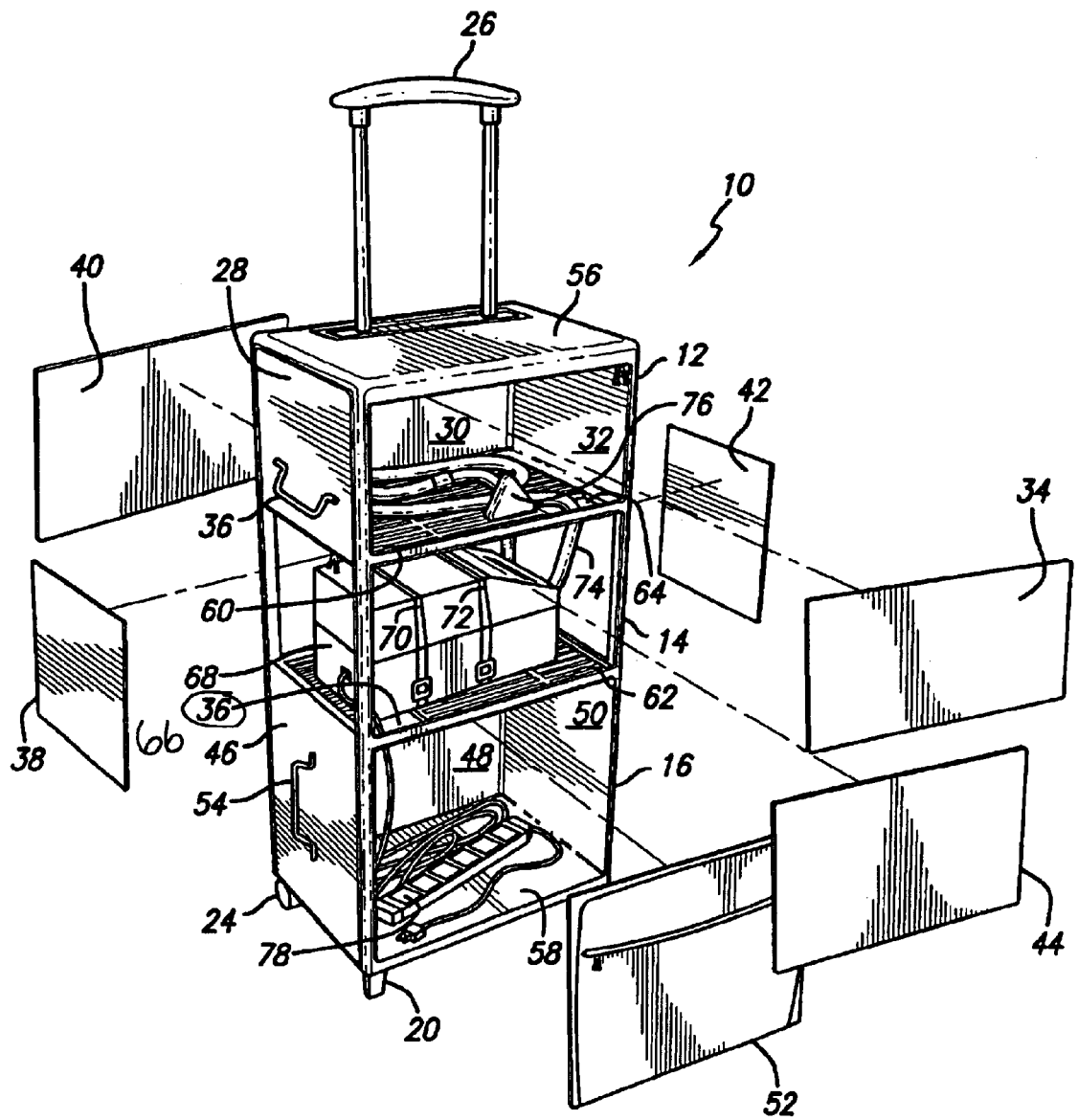
FIG. 2 is an exploded perspective view.

Referring now to the drawings there is shown in FIGS. 1–3 the medical device transporting unit 10, having three separate compartments, upper compartment 12, center compartment 14, and lower compartment 16. Unit 10 has two feet 18 and 20 and two wheels 22 (not seen) and 24, so that it can stand securely in the upright position and yet be rolled on wheels 22 and 24, by tilting unit 10 back and using retractable handle 26.

Upper compartment 12 is covered on all four sides by panels 28, 30 32, and 34. Side panels 28 and 32 have handles 36 and a similar handle on other side panel 32, for ease in carrying unit 10 when retractable handle 26 cannot be used. Back panel 30, as well as side panels 28 and 32 are fixedly attached and cannot be removed. Front panel 34 is totally removable, as shown in FIG. 2. Front panel 34 may be removably attached by any convenient means such as zippers, snaps or hook and loop fasteners.

Center compartment 14 is also covered on all four sides by side panel 38, back panel 40, opposite side panel 42, and front panel 44. All four panels of center compartment 14 are removable, for air cooling purposes, as explained in more detail below. The four panels of center compartment 14 are also removably attached by any convenient methods, such as zippers, snaps or hook and loop fasteners.

Lower compartment 16 has side panel 46, back panel 48, opposite side panel 50 and front panel 52. Side panel 46 has handle 54 to aid in carrying unit 10 when retractable handle 26 cannot be used. Panels 46, 48 and 50 are not removable, however front panel 52 is removable, in a similar manner to panels 34 and 44, to give access to lower compartment 16.

Unit 10 also has fixed top 56 and fixed bottom 58. Shelf 60, between upper compartment 12 and center compartment 14 is a grate, that is a frame of parallel bars. Shelf 62 between center compartment 14 and lower compartment 16 is also a grate. Shelf 60 has a cut-out opening 64 and shelf 62 has a similar cut-out opening 66, the purpose of which is explained below.

As shown in FIG. 2, a medical device 68 is carried in unit 10 by placing it on grated shelf 62 of center compartment 14. Medical device 68 is held securely on shelf 62 by any convenient tie-down means, such as elastic cords 70 and 72, which have hooks at each end to hook around a bar of grate shelf 62. This holds medical device 68 securely in place during transportation.

Depicted in the FIG. 2 is a CPAP machine 68, described above. It also comprises a hose 74 and a mask 76. By means of opening 64, hose 74 can remain attached to machine 68, pass through opening 64 and remain on shelf 60 during transportation, as well as during use. Hose 74 and mask 76 can also be tied down by any convenient means if desired, but do not necessarily have to be tied down.

Lower fixed shelf 58 is utilized to carry electrical cords and plugs 78 that are necessary for plugging machine 68 into a power outlet. Power cord 78 can remain attached to machine 68 by passing through opening 66 in center shelf 62. Lower compartment 16 is large enough for the user to also pack a few clothes or other items, as desired.

Figure 4:
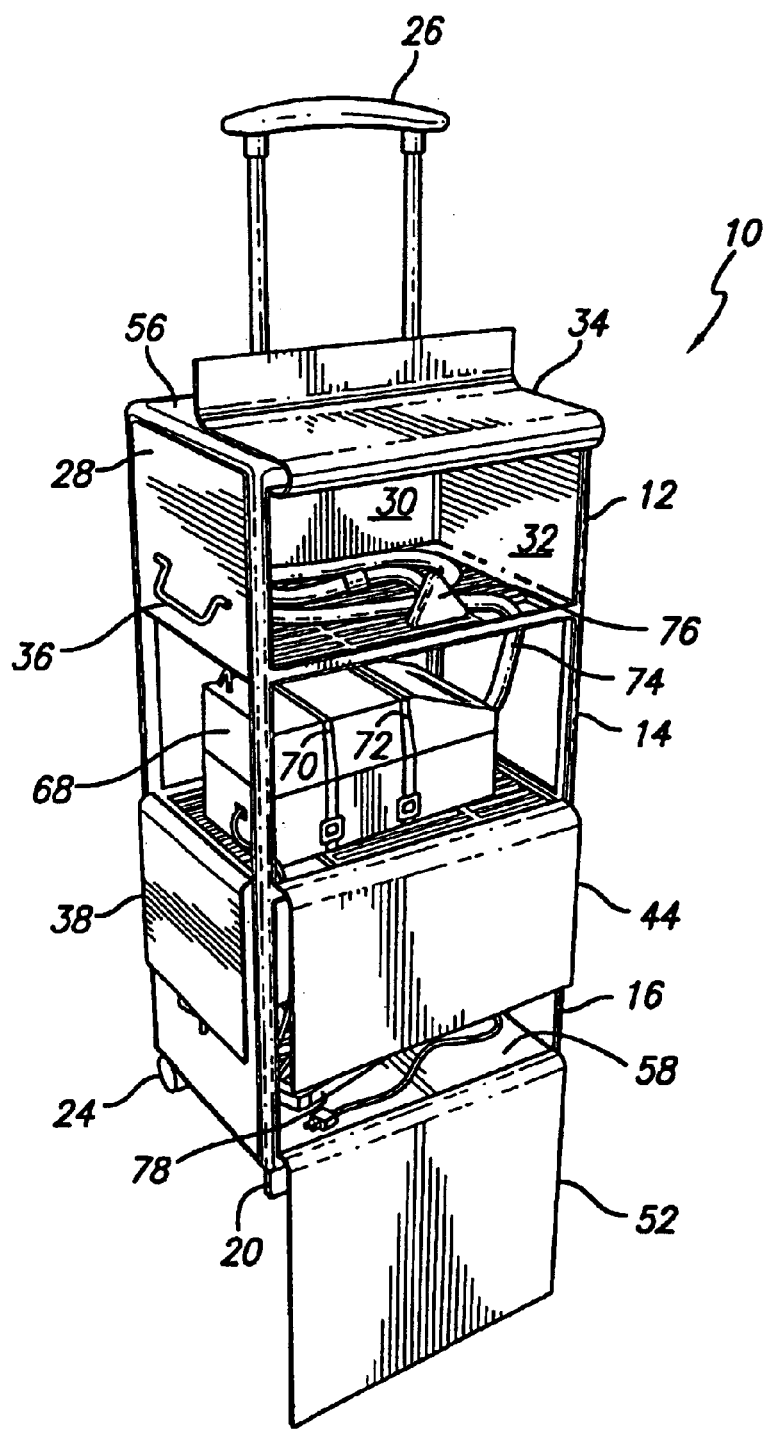
FIG. 4 is an alternate embodiment.

FIG. 4 shows the same unit configuration in which front panel 34 is removable on three sides but remains attached by a flexible hinge to top 56, so that in use, panel 34 can be folded over the top of top 56. All four panels 38, 40, 42 and 44, of center compartment 14, similarly remain attached by a flexible hinge and can be lowered against lower compartment 16 when the machine 68 is in use or when otherwise desired. Similarly, front panel 52 of lower compartment 16 remains attached at its lower end by a flexible hinge and can be lowered to rest against the ground during use. One advantage of this embodiment is that all the panels remain attached at least one edge, so that they cannot be lost.

All four panels of center compartment 14 need to be removed or lowered (FIG. 4) when the machine is in use, because machine 68 gets quite hot during use and needs as much air flow and exposure to the air as possible, to keep it cool. If a machine or other medical device which does not require cooling is being transported in unit 10, the panels of center compartment 14 do not all need to be removed, possibly only the front panel for access.

The unit of this invention provides a safe, secure, convenient and private method of not only transporting a medical device, such as a CPAP machine, but also allows the patient to use the medical machine while it remains stored in the unit, providing convenience and privacy. While a CPAP/BiPAP machine has been used in the description, examples of other medical devices that can be carried and transported by this unit include portable suction machines, portable oxygen tanks, nebulizer machines and humidifiers.

Having thus described the invention,

We claim:

1. A medical device transportation unit comprising an upper compartment, a center compartment and a lower compartment, all said compartments having a front panel, a rear panel and two opposite side panels, a fixed grated shelf of parallel bars between said upper compartment and said center compartment, a fixed grated shelf of parallel bars between said center compartment and said lower compartment, both of said grated shelves having a cut-out opening therein, the front panel of said upper compartment, the front panel of said lower compartment and all four panels of said center compartment being completely removable from said unit.

2. The transportation unit of claim 1 further comprising a retractable handle.

3. The transportation unit of claim 1 further comprising handles on both side panels of the upper compartment and the lower compartment.

4. The transportation unit of claim 1 in which all of the removable panels are attached to said unit by zippers, snaps, or hook and loop fasteners.

5. The transportation unit of claim 1 further comprising two wheels attached to the bottom of the unit.

6. The transportation unit of claim 1 in which all of said removable panels are fixedly attached to the unit along one edge of each panel by a flexible hinge.

7. The transportation unit of claim 1 further comprising tie-down straps removably attached to said grated shelves.

8. A continuous positive airway pressure machine transporting unit comprising an upper compartment, a center compartment and a lower compartment, all said compartments having a front panel, a rear panel and two opposite side panels, a fixed grated shelf of parallel bars between said upper compartment and said center compartment, a fixed grated shelf of parallel bars between said center compartment and said lower compartment, both said shelves having an opening cut-out therein, the front panel of said upper compartment, the front panel of said lower compartment and all four panels of said center compartment being completely removable from said unit, tie-down straps removably attached to said central compartment grated shelf, a continuous positive airway pressure machine held by said tie-down straps in said central compartment, a hose and mask in said upper compartment, said hose passing through said opening cut-out in the shelf between said upper compartment and center compartment, said hose attached to said continuous positive airway pressure machine in said central compartment, a power cord in said lower compartment, said power cord passing through said opening cut-out in the shelf between said center compartment and lower compartment, said power cord attached to said continuous positive airway pressure machine in said central compartment.

9. The transportation unit of claim 8 further comprising a retractable handle.

10. The transportation unit of claim 8 further comprising handles on both side panels of the upper compartment and the lower compartment.

11. The transportation unit of claim 8 in which all of the removable panels are attached to said unit by zippers, snaps, or hook and loop fasteners.

12. The transportation unit of claim 8 further comprising two wheels attached to the bottom of the unit.

13. The transportation unit of claim 8 in which all of said removable panels are fixedly attached to the unit along one edge of each panel by a flexible hinge.

\* \* \* \* \*